United States Patent [19]

Gammill

[11] Patent Number: 4,614,809
[45] Date of Patent: * Sep. 30, 1986

[54] ANTIATHEROSCLEROTIC FUROCHROMONES AND INTERMEDIATES THEREFOR

[75] Inventor: Ronald B. Gammill, Portage, Mich.

[73] Assignee: The Upjohn Company, Kalamazoo, Mich.

[*] Notice: The portion of the term of this patent subsequent to Aug. 18, 1998 has been disclaimed.

[21] Appl. No.: 603,533

[22] Filed: Apr. 25, 1984

Related U.S. Application Data

[62] Division of Ser. No. 378,686, May 17, 1982, Pat. No. 4,459,420.

[51] Int. Cl.$^4$ ............................................. C07D 311/78
[52] U.S. Cl. .................................................... 549/387
[58] Field of Search ......................................... 549/387

[56] References Cited

U.S. PATENT DOCUMENTS 3,470,165  9/1969  Fitzmaurice .................... 549/387
4,284,569  8/1981  Gammill ........................ 549/387

FOREIGN PATENT DOCUMENTS 761376  11/1956  United Kingdom ............. 549/387

OTHER PUBLICATIONS

L. R. Row, et al., Indian J. Chem. 5:105 (1967).

Primary Examiner—Nicky Chan
Attorney, Agent, or Firm—Lawrence T. Welch; Martha A. Cox

[57] ABSTRACT

The present invention particularly provides novel furochromones and intermediates for their preparation.

3 Claims, No Drawings

ANTIATHEROSCLEROTIC FUROCHROMONES AND INTERMEDIATES THEREFOR

CROSS REFERENCE TO RELATED APPLICATIONS

This is a division of application Ser. No. 378,686, filed 17 May 1982, now issued as U.S. Pat. No. 4,459,420 on 10 July 1984.

BACKGROUND OF THE INVENTION

The present application relates to novel furochromone compounds which are useful in the treatment of atherosclerosis. The use and preparation of these compounds is described in application Ser. No. 378,686, filed 17 May 1982, which is incorporated herein by reference.

PRIOR ART

Methods of the total synthesis of khellin are known, as are certain chemical intermediates useful in its synthesis.

The use of pyrogallol in the synthesis of khellin intermediates is known. For example, the transformation of pyrogallol to the khellin intermediate 1-(2,3-dihydro-6,7-dihydroxy-5-benzofuranyl)ethanone is known. The parahydroxylation of this intermediate is also known. See Row, L. R., et al., Indian J. Chem., 5:105 (1967) describing this transformation and the subsequent dimethylation to yield known khellin intermediates. U.S. Pat. No. 4,284,569 provides a variety of novel anti-atherosclerotic furochromones.

SUMMARY OF THE INVENTION

The present invention particularly provides:

(a) a benzofuran of formula III wherein $R_2$ is $C_1$–$C_4$ alkyl;

(b) a benzofuran of formula IV wherein $R_5$ is $C_2$–$C_4$ alkyl;

(c) a benzofuran of formula V wherein one of $R_6$ and $R_7$ is $C_1$–$C_4$ alkyl and the other is $C_2$–$C_4$ alkyl with the proviso that $R_6$ and $R_7$ are different; and (d) an anti-atherosclerotic furochromone of formula VI wherein one of $R_6$ and $R_7$ is $C_1$–$C_4$ alkyl and the other is $C_2$–$C_4$ alkyl with the proviso that $R_6$ and $R_7$ are different; wherein $R_{12}$ is —$CH_2$—$S(O)_n$—$R_{20}$, wherein n is zero, one or two and $R_{20}$ is $C_1$–$C_5$ alkyl;

wherein $R_{13}$ is:

(1) hydrogen; or (2) chloro, iodo, or bromo.

DESCRIPTION OF THE PREFERRED EMBODIMENTS

The present invention particularly provides 4-Ethoxy-9-methoxy-7-methylthiomethylfurochromone and 4-Methoxy-9-ethoxy-7-methylthiomethylfurochromone.

FORMULAS

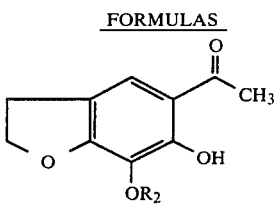

III

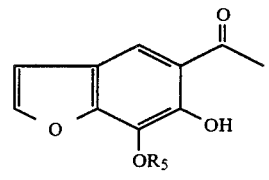

IV

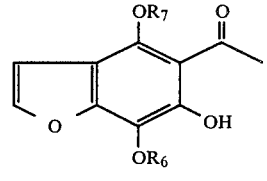

V

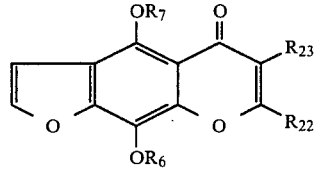

VI

I claim:

1. An anti-atherosclerotic furochromone of formula VI:

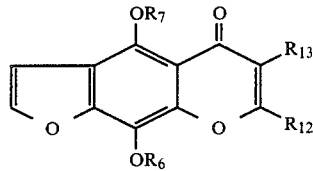

VI wherein one of $R_6$ and $R_7$ is $C_1$–$C_4$ alkyl and the other is $C_2$–$C_4$ alkyl with the proviso that $R_6$ and $R_7$ are different;

wherein $R_{12}$ is —$CH_2$—$S(O)_n$—$R_{20}$, wherein n is zero, one or two and $R_{20}$ is $C_1$–$C_5$ alkyl;

wherein $R_{13}$ is:

(1) hydrogen, or (2) chloro, iodo or bromo.

2. 4-Ethoxy-9-methoxy-7-methylthiomethylfurochromone, a compound according to claim 1.

3. 4-Methoxy-9-ethoxy-7-methylthiomethylfurochromone, a compound according to claim 1.

* * * * *

UNITED STATES PATENT OFFICE
CERTIFICATE OF CORRECTION

Patent No. 4,614,809          Dated 30 September 1986

Inventor(s) R. B. Gammill

It is certified that error appears in the above-identified patent and that said Letters Patent are hereby corrected as shown below:

Column 2, lines 27-34 should read:

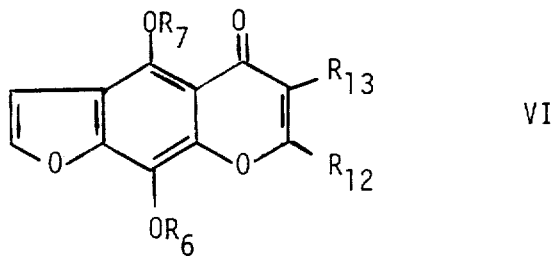

VI

Signed and Sealed this

Tenth Day of March, 1987

*Attest:*

*Attesting Officer*

DONALD J. QUIGG

*Commissioner of Patents and Trademarks*